United States Patent [19]
Edens et al.

[11] Patent Number: 6,117,433
[45] Date of Patent: Sep. 12, 2000

[54] USE OF COMPOSITIONS COMPRISING STABILIZED BIOLOGICALLY EFFECTIVE COMPOUNDS

[75] Inventors: Luppo Edens, Rotterdam; Hong Sheng Tan, Bleiswijk; Johannes Wilhelmus Jacobus Lambers, Pijnacker, all of Netherlands

[73] Assignee: DSM N.V., Te Heerlen, Netherlands

[21] Appl. No.: 08/930,685

[22] PCT Filed: Jan. 31, 1997

[86] PCT No.: PCT/EP97/00507

§ 371 Date: Apr. 8, 1998

§ 102(e) Date: Apr. 8, 1998

[87] PCT Pub. No.: WO97/27841

PCT Pub. Date: Aug. 7, 1997

[30] Foreign Application Priority Data

| | | | |
|---|---|---|---|
| Jan. 31, 1996 | [EP] | European Pat. Off. | 96200190 |
| Mar. 8, 1996 | [EP] | European Pat. Off. | 96200594 |
| Jun. 21, 1996 | [EP] | European Pat. Off. | 96201713 |
| Oct. 3, 1996 | [EP] | European Pat. Off. | 96202781 |

[51] Int. Cl.[7] ..................... A61K 9/14
[52] U.S. Cl. ............ 424/400; 424/57; 424/70.1; 424/94.3; 424/94.4; 424/94.5; 424/94.6; 424/94.63; 424/401; 424/489; 424/499
[58] Field of Search ............... 206/571; 424/57, 424/70.1, 94.1–94.67, 401, 489–491, 499, 484–488

[56] References Cited

U.S. PATENT DOCUMENTS

| | | | |
|---|---|---|---|
| 3,675,821 | 7/1972 | Morane et al. | 222/80 |
| 3,834,075 | 9/1974 | Nix et al. | 47/57.5 |
| 3,992,813 | 11/1976 | Fresher | 47/57.5 |
| 4,243,543 | 1/1981 | Guilbert et al. | |
| 4,556,554 | 12/1985 | Calvo | |
| 5,252,312 | 10/1993 | Gentile et al. | 424/44 |
| 5,827,506 | 10/1998 | McShane et al. | 424/59 |
| 5,843,409 | 12/1998 | Campbell et al. | 424/52 |

FOREIGN PATENT DOCUMENTS

| | | |
|---|---|---|
| WO 91 00094 | 1/1991 | European Pat. Off. |
| WO 91 09941 | 7/1991 | European Pat. Off. |
| WO 93 15726 | 8/1993 | European Pat. Off. |
| 0 710 478 | 5/1996 | European Pat. Off. |
| 6 318 M | 9/1968 | France |
| 41 21 820 | 1/1993 | Germany |

OTHER PUBLICATIONS

Database WPI, Week 7250, Derwent Publications Ltd., London, BG; AN 72–79393t, XP002031221 & SU 333 948 A (ND Zelinskii Organic Chem) 1972.

PDR –51 edition ABBOKINASE and UNASYN, 1997.

*Primary Examiner*—Neil S. Levy
*Attorney, Agent, or Firm*—Morrison & Foerster LLP

[57] ABSTRACT

A dual chambered dispensing system allows for application of an aqueous composition containing a biologically effective compound which is adequately stabilized. The system separately contains the stabilized biologically effective compound composition in one chamber and an aqueous basic composition in the other. Both compositions are simultaneously delivered from the dispensing system, whereupon the compositions are mixed to result in a final composition suitable for direct application.

26 Claims, 3 Drawing Sheets

USE OF COMPOSITIONS COMPRISING STABILIZED BIOLOGICALLY EFFECTIVE COMPOUNDS

This application is a national stage filing under 35 USC § 371 of international application No. PCT/EP97/00507, filed on Jan. 31, 1997.

FIELD OF THE INVENTION

The present invention relates to the field of application of compositions comprising stabilized biologically effective compounds by use of a multicomponent dispensing system.

BACKGROUND OF THE INVENTION

Topical application of enzymes has been described in the cosmetic as well as in the pharmaceutical field. For example, the use of proteases has been suggested to support or replace α-hydroxy acids in skin peeling preparations (Japanese patent application J04027388). Glutathion sulfhydryl oxidase has been identified as useful in hair-wave setting (Japanese patent application J04005220). Furthermore, International patent application WO93/19731 describes the use of glycosidases to enhance the process of skin desquamation and lysozyme has been mentioned to treat acne (HUT 057608). More recently, several patent applications using the enzyme transglutaminase have been published (WO94/18945, J02204407).

However, the limited storage stability of enzymes in liquid aqueous formulations is to be considered as the main limiting factor to the wider application of enzymes.

Commercial preparations containing enzymes often take advantage of the shelf stability of an enzyme in a dry state. According to such a concept, the easiest way to market an enzyme-containing product is by supplying the enzyme separately with the product, e.g. suitably packed as tablets. In an alternative approach, dry enzyme powder can be homogeneously dispersed into an essentially non-aqueous hydrophobic base, such as a suitable oil in combination with an oil gellant.

Disadvantage of the first approach is that the required dissolution of the enzyme tablet in an aqueous composition is slow and inconvenient. Regarding the second approach it should be noted that an enzyme requires water to be active. In order to be efficient, the mixing of an aqueous and an oily phase generally requires a relatively high energy input and cannot be achieved by simple hand-mixing. Thus, the mixing of an aqueous composition and a hydrophobic enzyme-containing phase is expected to be very inefficient.

The above problems can be circumvented by using aqueous stabilized enzyme compositions for topical applications. Unfortunately, aqueous enzyme formulations require high concentrations of water-miscible stabilizers intended to lower the water activity of the formulation. Polyols are often used for this purpose and long-term stability can only be effected by polyol concentrations well above 40% (v/v). However, enzymes often are not active in compositions containing high polyol concentrations. Especially the direct topical application of thus-stabilized enzyme composition will not provide sufficient water to reactivate the enzyme. Moreover, the presence of such high polyol concentrations in compositions for topical use is considered unacceptable.

Consequently, the high polyol concentration which is necessary to stabilize an enzyme in an aqueous environment prevents direct topical application of a thus-stabilized aqueous enzyme composition.

Another area in which enzymes can be advantageously used is the area of laundry hand wash applications. Although compared to machine washing the incidence of hand washing is very low in Europe and North America, hand washing remains popular as far as delicate fabrics are concerned. Of the delicate fabrics, the small category of woollen and silk items represents a particularly problematic area regarding stain removal, fabric depilling, colour revival and fabric shrinking. This category of specific fabrics may require specific enzymes, such as proteases active around a neutral pH value and/or at a low temperature or sulphur bridge rearranging enzymes like protein disulfide isomerase to counteract wool deformation stresses exerted during washing (EP 276547). A disadvantage of such niche products is that they obviously cannot bear the cost of extensive detergent or enzyme formulation developments.

Similarly, various biologically effective compounds other than enzymes are known which are unstable in aqueous end formulations, i.e. those formulations which are suitable for direct use in a specific application. Typically, biologically effective compounds like enzymes, antibiotics, vitamins, polyunsaturated compounds and the like, loose their activity upon prolonged storage in aqueous compositions. Although specific formulations are known in which said biologically effective compounds are stably incorporated, the latter formulations typically are not suitable for direct use in desired applications.

SUMMARY OF THE INVENTION

The present invention discloses a dispensing system separately containing a first and a second aqueous composition, said first composition being a composition comprising a biologically effective compound which is stably formulated, wherein said first and second composition generate a final composition when mixed upon dispensing, and wherein said final composition is effective to apply said biologically effective compound in an active form.

In the dispensing system of the invention, an aqueous composition comprising a stabilized biologically effective compound and an aqueous basic composition are separately contained. Using the dispensing system, simultaneous delivery of both aqueous compositions is allowed. Upon delivery, both compositions are mixed, resulting in a dilution of the composition comprising the stabilized biologically effective compound in the basic composition, generating a final composition suitable for direct application.

Preferred biologically effective compounds for use in the dispensing system of the present invention are enzymes, vitamins, polyene macrolide antibiotics, dihydroxyacetone, and aldehyde flavours. The dispensing system of the present invention is especially suitable for topical application of a biologically effective compound.

DETAILED DESCRIPTION OF THE INVENTION

In the dispensing system of the present invention, an aqueous composition comprising a stably formulated biologically effective compound and an aqueous basic composition are separately contained.

Using said dispensing system, simultaneous delivery of the aqueous composition comprising a stably formulated biologically effective compound (called the "effective composition" or "first composition" throughout the invention) and the aqueous basic composition (also called the "second composition") is possible. Upon delivery, both aqueous compositions are mixed, either in situ or in the dispensing system. Mixing of both compositions results in a final composition which contains a biologically effective compound in an active form and which additionally is suitable for direct use.

The term "basic composition" is used for a composition which produces in combination with the aqueous composition comprising the biologically effective compound a final composition which is suitable for direct application of the biologically effective compound. The nature of the basic composition mainly will depend on the desired application. Aqueous basic compositions are understood to include oil-in-water emulsions.

Preferably, the aqueous basic composition is a composition suitable for topical, detergent or cleaning use. More preferably, the aqueous basic composition is a composition suitable for topical use. Most preferably, the aqueous basic composition is a composition suitable for cosmetic use.

The aqueous basic composition can be a cream, a gel, a shampoo, a cleansing fluid, a lotion, a liquid detergent, a hard surface cleaning composition, and the like.

Biologically effective compounds which are suitable for use in the dispenser of the present invention are those compounds which display a biological activity and which are unstable in the aqueous end formulation in which the biologically effective compound should be applied. In addition, biologically effective compounds which are suitable for use in the dispenser of the present invention are those compounds for which a stable aqueous formulation is developed, which stable formulation is not suitable for direct use in the desired application.

The biologically effective compounds which are suitable for use in the dispenser of the present invention are distinguishable with respect to the source from which said compound is obtainable as well as with respect to the nature of said compound.

With respect to the source of the biologically effective compound, said compound is obtainable from an animal, a vegetable or a microbial source. Preferably, said compound is obtainable from a microbial or a vegetable source. More preferably, said compound is obtainable from a microbial source.

With respect to the nature of the biologically effective compound, said compound is selected from the group of primary and secondary metabolites, preferably from the group of enzymes, antibiotics, (poly)unsaturated compounds, vitamins, flavours, dihydroxyacetone, more preferably from the group of enzymes, vitamines, polyene macrolide antibiotics, aldehyde flavour compounds and dihydroxyacetone.

The instability of a biologically effective compound in an aqueous environment, which is particularly perceptible after prolonged storage, may be of a chemical nature, for instance caused by structural deterioration (e.g. denaturation in case of enzymes and other proteins), oxidative attack or other unfavorable conditions like non-optimal pH conditions. Oxygen, as well as light and the presence of metal ions from traces of iron or copper, are known for their detrimental oxidative effect on biologically effective compounds like vitamins, carotenoids, (poly)unsaturated oils and (poly)unsaturated fatty acids (see for example CRC Handbook of Food Additives, second edition). Instability may additionally be caused by microbial growth in an aqueous environment, or by physical instability of the aqueous composition containing the biologically effective compound.

Depending on the factor(s) causing instability of the biologically effective compound, stable aqueous formulations were developed which are characterized by, for instance, one or more of the following conditions: a low water activity, a low or a high pH, a high concentration of an antioxidant, a high concentration of a sequestering agent, a high concentration of an antimicrobial agent, crystallinity of the biologically effective compound, a high concentration of a viscosifying agent. Typically, said condition(s) necessary for stabilizing the biologically effective compound in an aqueous composition do(es) not allow the direct use of said aqueous composition.

The dispensing system of the invention enables the use of relatively high concentrations of chemical stabilizers to prepare stable formulations of inherently unstable biologically effective compounds, i.e. concentrations which can be much higher than those allowed in a final composition, since the stabilizers are diluted with an aqueous basic composition upon dispensing. Suitable stabilizing agents include water activity lowering agents like salts or polyols, sequestering agents like EDTA, phytate or gluconate or antioxidants like sulphites, glutathion, cysteine or ascorbic acid.

In another aspect of the invention, the use of the dispensing system ensures that the effective concentration of a biologically effective compound is reached after dilution of the effective composition in the basic composition. Therefore, the biologically effective compound can be present in the effective composition in a considerably higher concentration than would be required for efficacy. Several biologically effective compounds are insoluble in aqueous compositions in these higher concentrations. This implicates that the biologically effective compound can be present in a crystalline form. Said crystalline form is especially advantageous to ensure stability of the compound.

However, an important problem with compositions comprising crystalline compounds is that crystals tend to sediment in such compositions, i.e. said compositions are physically unstable.

The present invention discloses that sedimentation of a crystalline compound is prevented by the use of a suitable viscosifying agent. Said viscosifying agent preferably is able to form a three-dimensional network in an aqueous environment. More preferably, said viscosifying agent is selected from the group of xanthan, Carbopol® or related resins, or carrageenan. Most preferably, said viscosifying agent is xanthan. The concentration of a suitable viscosifying agent mainly is determined by the weight and size of the particles to be kept in suspension. Conveniently, the concentration may range from 0.1–3%, preferably from 0.2–0.6%.

The dispensing system of the present invention allows for the dilution of the stabilizing agent present in the composition containing a biologically effective compound upon dispensing with the basic composition. The dispensing system of the invention further allows for the dilution of the effective compound to its effective concentration.

The dilution factor of the composition containing a biologically effective compound (the effective composition) in the basic composition is adequately chosen, i.e. such that the end concentration of the stabilizing agent does not preclude application of the final composition and such that the biologically effective compound is present in the final composition in its appropriate effective concentration. The dilution factor is determined by the ratio in which the effective composition and the basic composition are delivered by the dispensing system. Preferably, the ratio between the effective composition and the basic composition varies from 1:1 to 1:50, more preferably from 1:2 to 1:20, most preferably the ratio is 1:5 to 1:10.

According to the invention, the viscosity of the effective composition preferably has a value which is comparable to the viscosity of the basic composition which is applied simultaneously with the composition containing the biologically effective compound. For instance, both compositions can have a lotion-like, a cream-like or a gel-like consistency. The viscosity of the effective composition additionally will depend on the type of dispensing system which is used to deliver the compositions. For instance, the use of a tube requires a relatively high viscosity of both compositions.

The amount of viscosifying agent to be added to the effective composition will depend among others on the desired viscosity of said composition. Any viscosifying agent known to the skilled person which is compatible with the final composition as well as the desired application can be used. For instance, for topical application its acceptability for topical use should be considered. Examples of viscosifying agents include carrageenans, cellulose derivatives, polyacrylic acids, clays, polyethylene glycols, hydrocolloids such as xanthan.

If desired, agents can be added to the effective composition and/or the basic composition, such that both composition have the same or have a different appearance. A typical example of such an agent is a colourant.

The aqueous effective composition is understood to include oil-in-water emulsions.

To obtain a desired shelf stability of compositions containing biologically effective compounds which are prone to oxidation, non-translucent packaging material with a low ingress of oxygen would be desirable. The dispensing system of the present invention provides the option to pack the composition containing the biologically effectice compound in a compartment made from non-translucent material with very low oxygen permeation rates even under conditions of high humidity, to minimize the effect of light and ingress of oxygen. Preferred packaging materials include PVdC, EVOH and alumina-coated polymers (see Food Manufacture, June 1991, pp 49–53). If applied in larger volume dispensers, the use of an air-free lotion pump to dispense the biologically effective compound is another requirement.

The dispensing sytem to be used in the method of the invention is not critical to the invention. The present invention contemplates any system which allows for the separate containment of the stabilized effective composition and the basic composition. Separate containment is understood to include any form of separation which is able to prevent a substantial diffusion of water from one to the other composition.

For instance, a dispensing system can be selected from the multicomponent dispensing systems which have been developed for the packaging and delivery of non-compatible chemical compounds, i.e. chemical compounds which react with each other when brought into contact. For instance, multicomponent dispensers are known from the field of adhesives. The packaging of multicomponent adhesives requires complete separation of the resin and the hardener. Yet, convenience in use requires simultaneous delivery of the two components.

Apart from adhesives, multicomponent dispensing systems have also been described for the formulation of incompatible compounds in toothpaste. Flexible two-compartment dentrifice tubes are described in U.S. Pat. Nos. 4,487,757, 4,098,435 and U.S. 4,211,341. The latter patent discloses the use of extrudable materials such as carboxymethylcellulose gel in a polyhydric alcohol solution to separate the incompatible compounds. A two-compartment tube for the storage of a non-aqueous enzyme composition separate from the aqueous toothpaste composition has been described in FR 2,051,922.

In yet another but basically very simple approach, one pair of plastic pouches provides material for single use only. The outlets of the two pouches are close to each other and discharge of the contents can be effectuated by tearing open the end pieces of the pouch (German patent application DE 3 630 849).

The present invention also contemplates the formulation and storage of the stabilized effective composition and the basic composition in separate containers, which are put together and/or provided with a suitable dispenser by the user. It is also possible that a dispensing system already provided with a container containing one composition, e.g. the stabilized effective composition, is additionally provided with a container with the other composition, e.g. the basic composition.

The dispensing system of the present invention can be conveniently used for any application wherein the action of a labile biologically effective compound is desired. In particular, the dispensing system of the invention provides a convenient and simple way for topical application of a biologically effective compound of interest. Topical application is understood to include application on skin and hair and application in the oral cavity, e.g. on teeth.

The applicability of the dispensing system of the present invention is now illustrated in the light of several biologically effective compounds.

Enzymes

Typically, an aqueous enzyme composition is stabilized with a high concentration of a water activity lowering agent, such as a polyol or a salt. Preferably, a polyol is used for stabilization.

Using the dispenser of the present invention, the mixing of the enzyme and the basic composition results in an actual dilution of the enzyme composition in the basic composition. The high concentration of for instance a polyol in the enzyme composition guarantees activity of an enzyme upon dilution, even after a prolonged storage period of the enzyme composition.

Said dilution of the enzyme composition results in a dilution of the polyol, which on its turn results in a reactivation of the enzyme. Depending on the enzyme and the polyol used, enzyme reactivation can be expected to start at polyol concentrations below 40% w/w.

The ratio in which the enzyme composition and the basic composition are delivered by the dispensing system depends for instance on the concentration of the polyol in the enzyme composition, whereby the ratio should be adjusted in such a way to ensure reactivation of the enzyme. Furthermore, if topical use is desired, said ratio should be adjusted in such a way that the concentration level of the polyol, after mixing the enzyme with the basic composition, does not exceed the acceptable level for use in topical formulations.

Use of the dispensing system of the invention enables the stable formulation and application of any enzyme of interest. Preferably, the enzyme of interest belongs to the class of oxidoreductases, transferases, hydrolases or isomerases. More preferably, the enzyme is a glucose oxidase, peroxidase, lipoxygenase, superoxide dismutase, tyrosinase, protease, phosphatase, phytase, glycosidase, glucanase, mutanase ($\alpha$-1,3-glucanase), dextranase, lysozyme, lipase, phospholipase, sulfatase, urease, transglutaminase or protein disulfide isomerase. It is also possible to apply a stabilized composition comprising a mixture of two or more enzymes.

The concentration of the enzyme in the enzyme composition mainly will be determined by the type of application.

The present invention also envisages enzyme compositions in which the enzyme is formulated in a particle form. Enzymes formulated as particulate matter greatly reduce the risk of sensitization which may occur upon potential inhalation of enzyme molecules when dried after application. Preferably, the enzyme is formulated as particles having a particle size of at least about 5–10 μm. The upper limit of the particle size of the enzyme particles generally will be determined by the fact that larger particles will have an unfavourable surface loading and may produce a gritty feeling upon application to the skin. Conveniently, the upper limit of the particle size is about 100 μm.

One method to obtain enzyme particles of at least about 5–10 μm is to covalently immobilize the enzyme on a suitable carrier, as described in e.g. Methods in Enzymology, vol. 44 (1976). Another example of a suitable particle form is a so-called ChiroCLEC (Altus Biologics Inc., Cambridge, Mass., USA), which consists of cross-linked enzyme crystals. These cross-linked enzyme particles do not need the presence of high concentrations of a water activity lowering agent such as a polyol for stable formulation; they are chemically stable in an aqueous composition because of their crystalline form. Nevertheless, water activity lowering agents may still be added to improve microbiological stability of the aqueous composition.

The choice of the polyol which is used to stabilize the enzyme composition is not critical for the invention. Any polyol which is known to the skilled person to effectively stabilize enzymes in aqueous solutions can be used. Polyols that are particularly useful are polyols selected from the group of glycerol, sorbitol, propylene glycol, maltodextrins, or a sugar such as sucrose, lactose, glucose or trehalose. For topical applications, one should consider a polyol which is acceptable for topical use, i.e. glycerol, polyethylene glycol, butylene glycol, propylene glycol, trehalose or sorbitol.

The polyol is used in a high concentration, i.e. a concentration which results in a sufficiently low water activity in the enzyme composition to adequately stabilize the enzyme. It is known in the art that these concentrations may somewhat vary with the polyol used. Preferably, the polyol is used in a concentration of 20–90%, more preferably in a concentration of 30–90%, even more preferably in a concentration of 40–90%, even more preferably in a concentration of 50–90%, most preferably in a concentration of 60–80%.

A low water activity in an aqueous composition is also advantageous for preventing microbial growth in the composition.

In addition to a polyol, a salt such as NaCl may be used to enhance the stability of the enzyme during the product's shelf life. To further improve enzyme stability, low concentrations of enzyme stabilizers such as reducing agents, calcium salts or substrate or substrate-related ligands may be added (Gray, 1993, in: Thermostab. Enzymes, pp. 124–143. Narosa, New Delhi).

Optionally, a viscosifying agent may be added to the enzyme composition, in particular if the viscosity of the enzyme composition due to the polyol or other relevant components is not as high as is desirable. The amount of viscosifying agent to be added to the enzyme composition will depend on the viscosifying properties of the polyol which is used for stabilization of the enzyme composition as well as on the desired viscosity of the enzyme composition.

If an immobilized or crystalline enzyme preparation is used, the viscosity of the enzyme composition should be such that sedimentation of enzyme particles is prevented.

Preferably, as is indicated before, a viscosifying agent is used which is able to form a three-dimensional network in an aqueous composition.

According to the invention, the enzyme composition will be essentially simultaneously delivered with an appropriate aqueous basic composition. The nature of this aqueous basic composition is not critical for the invention, but will mainly depend on the type of application which is desired.

Attention should further be paid to avoid that the aqueous basic composition contains components that can be expected to inactivate enzymes instantaneously For cosmetic lotions, a typical example of a component expected to inactivate enzymes is ethanol in high concentrations.

The dispensing system of the present invention can be conveniently used for any application wherein the action of an enzyme is desired. In particular, the dispensing system of the invention provides a convenient and simple way for topical application of an enzyme of interest. A preferred enzyme for topical use of the dispenser of the invention is a protease.

The dispensing system of the invention is also suitable to simultaneously deliver an enzyme composition and a second composition comprising a proactive substrate, whereby the enzyme converts the proactive substrate into an active ingredient upon delivery and mixing of both compositions. This embodiment of the invention is preferred when the active ingredient is unstable in a particular composition and the possibility exists to formulate a precursor of the active ingredient, the so-called proactive substrate, which is more stable.

For instance, vitamin E-acetate, vitamin A-acetate and vitamin A-palmitate represent precursor molecules typically used to apply these unstable but desirable vitamins on the skin. Due to enzymatic activity in or on the skin, part of the precursor is believed to be slowly converted into the active compound (see for example: Boehnlein et al., Pharmaceutical Research Vol. II, no. 8 (1994), 1155–1159). Following the enzyme dispensing method of the invention, combining such shelf stable precursors and the appropriate hydrolytic enzymes, active retinol or tocopherol could be released on the skin. An important advantage of the use of the dispensing system of the invention is that the hydrolysis rate of the precursor molecules significantly is increased as compared to the situation where one depends on relevant enzymes which are present in the skin. In certain applications, e.g. in anti-sunburn applications, the benefits of an instantaneous release of the desired concentrations of vitamin A are evident (see for example Beijersbergen van Henegouwen et al, Fat Sc. Technol. 94 (1992), 24–27).

To activate palmitate derivatives of either vitamin A or vitamin E, the use of a suitable lipase is an obvious choice. It can be expected that many of the commercially available lipolytic enzymes will be able to hydrolyse these precursor molecules into the active vitamin and palmitic acid. However, the use of a lipase in cosmetic applications has some serious disadvantages including the breakdown of oils present in cosmetic compositions and the degradation of a considerable portion of the protective lipid compounds present on the human skin (Cosmetics & Toiletries 102 (1987), 36–42). To avoid this undesirable situation it is advantageous to use acetate rather than palmitate derivatives of the respective vitamins, enabling the use of enzymes which are capable to selectively remove the acetate moiety of the vitamin precursor without attacking skin lipids.

For example, certain esterases/lipases have a preference for short-chain acyl groups (from 2–10 carbon atoms) and are not capable to hydrolyze longer ($\geq 16$ carbon atoms)

fatty acyl groups. Such esterases are commercially available from for instance Recombinant Biocatalysis Inc. (Philadelphia, USA). In addition, xylan acetylesterase (cf. EP 507369) and rhamnogalacturan acetylesterase (cf. WO 93/20190) are active towards plant cell wall components and unlikely to hydrolyse lipids present on the human skin. Apart from this category of enzymes, esterase activity has also been attributed to certain serine proteases. The use of a suitable serine protease in this application is advantageous because it allows the combination of a skin peeling effect with the simultaneous conversion of a selected vitamin precursor.

Another vitamin, ascorbic acid, has claimed benefits in cosmetics because of its inhibitory effect on melanin formation in human skin, its stimulation of collagen formation and its antioxidant activity. Unfortunately, ascorbic acid cannot be applied to any cosmetic product because of its poor stability. Therefore, magnesium ascorbyl phosphate, a stable and water-soluble ascorbic acid derivative, has been developed and commercialised by several companies. Due to the presence of fosfatase enzymes on the skin, magnesium ascorbyl phosphate can be converted in the active but unstable ascorbic acid in situ. Unfortunately, the activity of fosfatase enzymes which naturally occur on the skin is rather low (Mima et al. Vitamins 41 (1970), 387). The dispensing system of the invention enables the combination of ascorbyl phosphate and a suitable phosphatase to ensure rapid formation of ascorbic acid on the skin. The enzyme phytase, catalyzing the release of phosphate from inositol-hexakisphosphate (phytate), in particular the phytase from *Aspergillus niger*, appears to be a very suitable phosphatase in this regard.

Very similar to the approach in which proactive vitamin derivatives are activated by the in situ removal of the stabilizing moiety of the derivative, other types of precursor molecules can be enzymatically modified. Several glycosylated natural colourants are known including anthocyanins and the food grade carmine red. As described by Blom (Food Chemistry 12 (1983), 197–204), the combination of β-glucosidase and red anthocyanin pigment results in a water-insoluble, coloured aglycon. Using the dispensing system of the invention, the aglycon is formed upon dispensing and mixing of a stabilized β-glucosidase-containing composition and a suitable cosmetic composition containing a red anthocyanin. Due to its increased hydrophobicity, the aglycon will adhere more tightly to hydrophobic surfaces like skin and hair and therefore is removed less efficiently by water from these surfaces.

Other enzymatic approaches are aimed at generating reactive colourants for oxidative colouring of hair using the dispensing system of the invention. To this end, a stabilised laccase composition is combined with a suitable composition containing a colourant precursor, for example a mono- or polyphenolic compound (see e.g. FR 2,694,018; EP 504005).

The dispensing system of the invention is also advantageously used for the in situ peroxidase-mediated formation of bactericidal compounds. Separate containment of the stabilized peroxidase on the one hand and suitable precursor molecules, optionally plus cleaning agents, on the other hand is essential for the application of certain bactericidal agents with a limited period of bacteriological activity (cf. U.S. Pat. Nos. 4,476,108, 4,588,586). Typical examples of such naturally occurring biocidal compounds are hypohalous acids produced by haloperoxidases from hydrogen peroxide plus halides and hypothiocyanate produced by lactoperoxidases from hydrogen peroxide plus thiocyanate.

In all cases, hydrogen peroxide is an essential but rather unstable precursor.

Hydrogen peroxide solutions can be stably incorporated in the second aqueous composition in the dispensing system of the invention, by the use of stabilizers such as sodium stannate or phosphonic acid (e.g. Dequest 2010). These stabilizers preferably are combined with a suitable viscosifying agent like Carbopol 934 or Rheovis CRXCA (Allied Colloids). In this approach, the first composition contains the stabilized enzyme and any hydrogen peroxide-incompatible chemicals.

The dispensing system of the invention also enables enzymatic in situ generation of hydrogen peroxide by a hydrogen peroxide generating enzyme, for instance an alcohol oxidase. Said hydrogen peroxide generating enzyme is incoporated in the same composition as the peroxidase. This form of mild disinfection, optionally combined with cleaning, is an issue not only in the field of topical application, to fight various forms of eczema or acne, but also in applications such as contact lens cleaning and household hard surface cleaners.

The in situ generation of lipoperoxides is further example of the use of the dispenser of the invention. To this end, a stabilized lipoxygenase composition and a linoleic acid-containing composition are separately contained and mixed upon dispensing. It is also possible to formulate the lipoxygenase and linoleic acid in one composition, since the high polyol concentration used to stabilize the enzyme additionally ensures inactivity of the enzyme. In situ generated lipoperoxides are suitable for topical application, e.g. for dehairing or inhibition of hair growth (Puig Muset et al., Arzneimittel & Forschung, 10 (1960), 234–239).

It is also possible to combine a first composition comprising an enzyme with a second composition comprising an additional active ingredient, whereby said additional active ingredient also displays a desired activity in the application in question. For instance, synergy may exist between the enzyme and the additional active ingredient.

For a totally different application than topical application, I.e. bread making, a dispenser is used combining baking enzymes, e.g. amylases, hemicellulases, protein disulphide isomerase, lipoxygenase and other redox enzymes, on the one hand and additional components of a fluid bread improver on the other hand, whereby the suitable enzyme substrates are present in the dough.

An example of a combination which may create synergy is the combination of a protease and a keratinolytic agent, such as an α-hydroxy acid. The so-called fruitacids (α-hydroxyacids or AHA's) have emerged in the cosmetic industry as agents that can induce skin peeling and thus achieve anti-aging benefits. A disadvantage is that the low pH values required for high cell renewal rates are accompanied by irritation phenomena (see Smith, W. P., Cosmetics & Toiletries Vol 109, pp 41–48, 1994). To minimize irritation, one strategy can be to lower either the AHA concentration or to increase the pH of the cosmetic composition and to compensate for the reduced skin peeling effect by adding a proteolytic enzyme to the composition.

Another example is found in the area of teeth care products. As from the introduction of dentifrices with fluoride compounds, the incidence of dental caries has been dramatically diminished through fluoride mediated reinforcement of the tooth enamel layer. As a result, the bacterium Streptococcus mutans growing in dental plaque emerges as one of the main residual causes for caries. Effective removal of *S. mutans* is only possible by dissolving the protective and water-insoluble polysaccharide matrix by which *S. mutans* adheres to the enamel (see for example Hamada and Slade, Microbiol. Rev. 44 (1980), 331–384). As disclosed in US 4,438,093, enzymes such as mutanase and dextranase prevent and suppress plaque formation. Therefore, the enzyme dispensing method of the invention provides a convenient way to combine a fluoride-containing dentifrice with a polyol-stabilized polysaccharide degrading enzyme composition.

The dispensing system according to the invention can be advantageously used in other applications than topical use. An example is in laundry hand wash applications for delicate fabrics, such as wool. In the dispensing system according to the invention, a simple liquid detergent and a stabilized enzyme composition are separately contained, to be simultaneously dispensed in the desired ratio.

Polyene Antibiotics

The development of stable aqueous compositions comprising polyene macrolide antibiotics, such as natamycin, nystatin and amphotericin-B, always has been problematic, since these antibiotics are extremely unstable in aqueous solutions.

For the treatment of fungal infections with natamycin, natamycin compositions with a relatively high concentration of solubilized natamycin are required, in particular because fungi require a relatively high minimal inhibitory concentration. Typically, natamycin has a relatively high solubility in organic solvents like dimethylformamide, DMSO, glycerol or propylene glycol, or in aqueous compositions at either a low or a high pH. To obtain aqueous compositons with a high concentration of solubilized natamycin, this antibiotic preferably is solubilized under acid or base conditions. However, the stability of natamycin under these conditions is rather poor. Therefore, such natamycin preparations are preferably made just before use.

For instance, in Dutch patent application NL 7613253, the combination of natamycin with citric acid is described for the treatment of horses and cows suffering from trichophyton infections, whereby the solution for the treatment must be prepared just before use by adding an appropriate amount of water to a solid mixture of natamycin and citric acid. However, the solid mixture of natamycin and citric acid is very hygroscopic and therefore also stable for only a rather short period.

Stable aqueous natamycin compositions are described in European Patent Application EP 678241 which is incorporated herein by reference. The stable natamycin compositions disclosed in EP 678241 are suspensions of natamycin crystals in an aqueous medium, wherein sedimentation of the crystals is prevented by the addition of a suitable viscosifying agent.

Stable natamycin compositions, for instance those disclosed in EP 678241 can be advantageously used in the dispensing system of the invention. A simultaneous dosage of a stable natamycin suspension and a suitable basic composition is possible. When a final formulation with a high amount of solubilized natamycin is required, said suitable basic composition preferably is a composition having either a low or a high pH.

Fungal skin infections in humans also form a potential target for natamycin treatment, provided that a suitable formulation of natamycin is available. Suitable formulations of natamycin to fight these infections include compositions comprising a combination of natamycin with citric acid. The use of a dispensing system according to the invention enables the combination of a stable aqueous natamycin suspension with a second citric acid containing composition.

Another example of a suitable basic (second) composition is an anti-dandruff shampoo.

Other Compounds

Dihydroxyacetone (DHA) is produced by fermentation and is the active ingredient of cosmetic products imparting artificial tan to the human skin. It was recognized a long time ago that DHA is rather unstable in aqueous solution, said instability resulting in loss of skin tanning capability as well as in the formation of skin-irritating agents such as formaldehyde and formic acid.

Stable DHA solutions are obtained by adjusting the pH of a DHA solution to the lower ranges, preferably to a value below pH 3. As these acidic pH values are incompatible with topical use, it would be advantageous to incorporate a composition for topical use, e.g. a cosmetic composition, and the DHA-containing acidic composition in a dispensing system according to the invention. The stable acidic DHA composition is neutralised upon mixing with a larger volume of a well buffered cosmetic composition.

Aldehyde flavour compounds are among the most unstable flavour compounds, especially under basic conditions. As a consequence, it is a main problem how to stably incorporate flavour aldehydes, like geranial, neral and citronellal, in personal care products with a basic character, like lotions, fluid soaps and shampoos.

The dispensing system of the invention conveniently ensures a separate containment of a flavour-containing composition and a suitable cosmetic composition, thus enabling application of desirable flavour compounds in personal care products.

EXAMPLE 1

Figure 1:
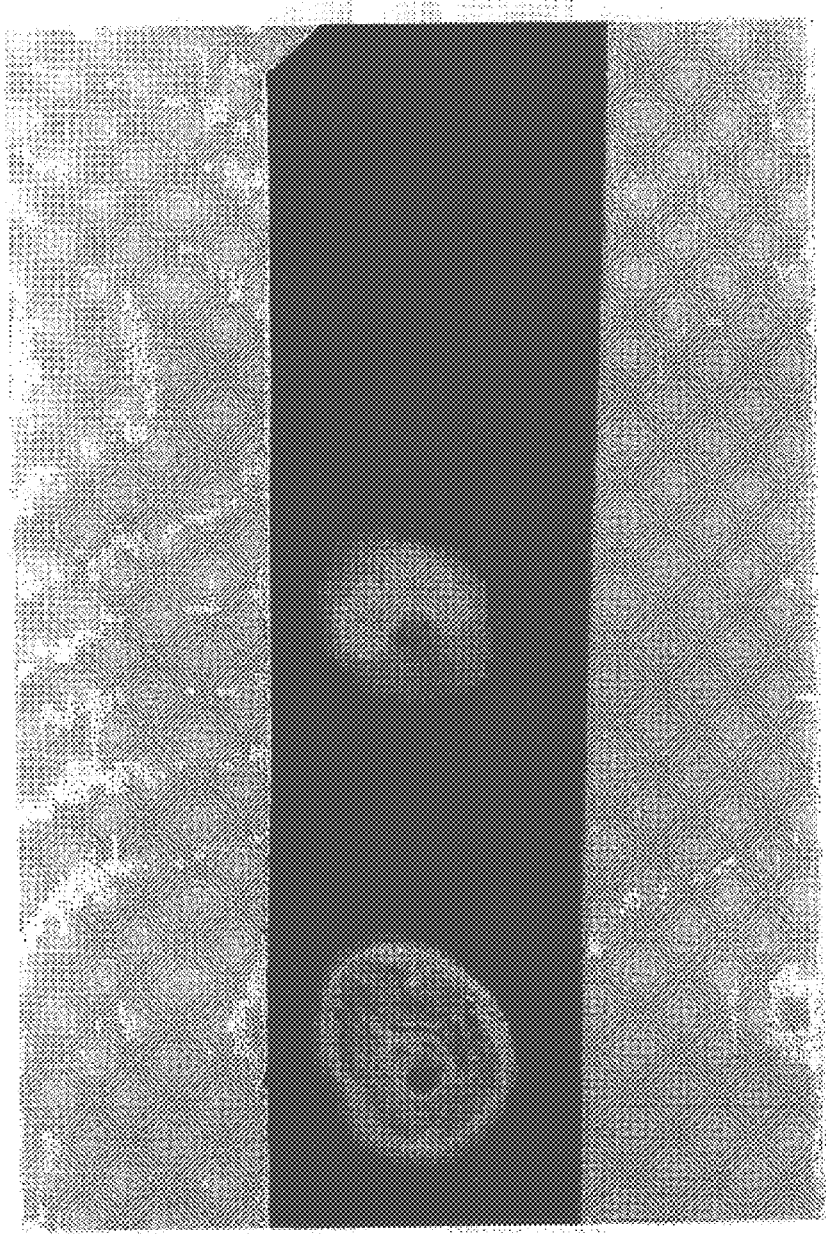
FIG. 1 shows the proteolytic activity of plain and diluted stabilized aqueous protease compositions. Proteolytic activity is measured as a clear spot on a gelatin covered film plate.

Storage Stability of Proteases in Compositions Comprising Different Types of Polyols To illustrate the storage stability of various neutral proteases in different types of polyols, partially purified proteases from different sources were dissolved in liquids containing 70% (w/w) of either butylene glycol, propylene glycol or PEG 6000 and stored at either 5° C., 25° C. or 40° C. At various time intervals, after dilution in aqueous buffer, remaining enzyme activities were measured.

Enzymes Used

Serine protease powder from *Bacillus licheniformis* was obtained from Genencor International, Brughes, Belgium.

Neutral protease non-standardised (metallo-protease from *Bacillus amyloliquefaciens*) was obtained from Gist-brocades, Séclin, France.

Stabilized enzyme formulations containing either Serine protease or Neutral protease were prepared by dissolving the required quantities of enzyme powder in either 70% (w/w) butyleneglycol (1,3-butane diol; BG), propylene glycol (1,2-propanediol; PG) or PEG 6000 (polyethylene glycol 6000; PEG). To each solution, calcium acetate pH 6.0 was added to a concentration of 0.1%, for maximal enzyme stability. Any resulting precipitate was removed by centrifugation after which the variously stabilized enzyme solutions were stored at either 5° C., 25° C. or 40° C. At various time intervals samples were taken and tested for residual Serine and Neutral protease activity. More than thousand-fold dilution of the polyol containing enzyme formulations in the protease test guaranteed the absence of non-protease related interactions from chemical contaminants.

Enzyme activities were determined following the Gist-brocades protocol for neutral protease activity. This procedure (ISL Method Number 61195) is available from Gist-brocades Delft upon request. Briefly, the procedure is as follows:

A strongly diluted enzyme solution is added to a solution of 0.3% Hammersten casein at 40° C., pH 7.0. After incubation during 60 minutes, protease activity is stopped by the addition of TCA. After thorough mixing and an additional incubation at 4° C. for 30 minutes, the samples are centrifuged. Extinction of the clear supernatant is measured at a wavelength of 275 nm against distilled water. By comparison with reference protease samples, the final protease activity is obtained.

Conclusions

Serine protease dissolved in either 70% butylene glycol or propylene glycol is more stable than neutral protease.

Butylene glycol and propylene glycol are clearly superior to PEG 6000 in enzyme stabilization.

|  | Weight (g) | End concentration |
|---|---|---|
| Stabilized enzyme formulation | | |
| Water | 24.25 | 48.5% |
| Neutral protease | 25 mg | |
| Propylene Glycol | 25.0 | 50% |
| Hydroxypropyl Cellulose | 0.75 | 1.5% |
| (Klucel type H from Hercules) | | |

Preparation: after mixing the viscosifying agent hydroxypropyl cellulose with the propylene glycol, water in which the enzyme is dissolved is added and mixed overnight.

| Aqueous formulation | | |
|---|---|---|
| Water | 48.5 | 97% |
| Hydroxypropyl cellulose | 0.75 | 1.50% |
| Propylene Glycol | 1.0 | 2% |

Preparation: hydroxypropyl cellulose and propylene glycol are mixed, subsequently added to the water and mixed overnight.

A certain amount of the stabilized protease formulation (plain or diluted with the aqueous formulation) is spotted on Agfapan 25 film plate. If the enzyme is active, the gelatin on the film plate will be proteolysed, leaving a more or less clear spot. This assay mimics the ability of protease to degrade the rough top layer of keratin in vivo.

TABLE 2

Serine protease

RESIDUAL PROTEOLYTIC ACTIVITY AT:

| | 5° C. | | | 25° C. | | | 40° C. | | |
|---|---|---|---|---|---|---|---|---|---|
| Days | BG | PG | PEG | BG | PG | PEG | BG | PG | PEG |
| 1 | 9670 | 10050 | 9970 | 9670 | 10050 | 9970 | 9670 | 10050 | 9970 |
| 9 | 9590 | 9840 | 9980 | 9770 | 9940 | 8420 | 9460 | 9580 | 2530 |
| 22 | 9390 | 9600 | 9500 | 9088 | 9540 | 4620 | 9120 | 9440 | 2030 |

TABLE 3

Neutral Prctease

RESIDUAL PROTEOLYTIC ACTIVITY AT:

| | 5° C. | | | 25° C. | | | 40° C. | | |
|---|---|---|---|---|---|---|---|---|---|
| Days | BG | PG | PEG | BG | PG | PEG | BG | PG | PEG |
| 1 | 17900 | 18500 | 5690 | 17900 | 18500 | 5690 | 17900 | 18500 | 5690 |
| 9 | 16900 | 16600 | 3580 | 15900 | 14600 | 1660 | 3840 | 2540 | <2000 |
| 22 | 16300 | 17600 | 3370 | 15200 | 12600 | 2930 | <2000 | 4410 | <2000 |

EXAMPLE 2

Reactivation of Protease from a Stabilized Formulation

Materials

Neutral Protease from *B. amyloliquefaciens*, non-standardized, was obtained from Gist-brocades Séclin (France).

After incubation of the film plate with the plain stabilized protease formulation no clear spot is observed, indicating that the protease is not active due to the high concentration of polyol. A 1:1 and a 1:2 dilution of the stabilized protease formulation with the above aqueous formulation, yielding propylene glycol concentrations of 26% and 18%, respectively, results in a clear spot with a diameter increasing with the dilution factor, indicating reactivation of the protease (see FIG. 1). Although the 1:1 dilution already results in a partial reactivation of the protease, the concentration of the polyol is still too high to be acceptable for topical use.

A non-stabilized enzyme preparation, i.e. without propylene glycol, appeared to be inactive in about one week.

Thus, enzymes stabilized according to the invention are essentially inactive until reactivated by dilution with an appropriate composition.

EXAMPLE 3

Proteolytic Activity in Compositions Comprising Different α-hydroxyacids

This example illustrates the efficacy of a number of protelytic enzymes under acid conditions and in the presence of α-hydroxyacids (AHA's). Protelytic activity was assayed on photographic gelatin film.

Enzymes and Materials Used

Serine protease powder from *Bacillus licheniformis* was obtained from Genencor International, Brughes, Belgium and dissolved in a mixture of 35% (w/w) butylene glycol, 35% (w/w/) glycerol, 0.1% (w/w) $Ca(Ac)_2$ pH 6.0 and water. Enzyme activity in solution was adjusted to obtain an activity of approx. 500 Neutral Protease Units at 37° C., pH 7.0 (see Example 1).

Aspartic proteinase liquid from *Rhizomucor miehei* (210–000 milk clotting units/ml) was obtained from Gist-brocades, Séclin, France.

Cysteine proteinase powder from papaya fruits (60 million papain units/gram, assayed according to Food Chemical Codex III) was obtained from Gist-brocades, Séclin, France. Prior to use a solution of cysteine proteinase was freshly prepared by dissolving 20 mg of enzyme powder in 2 ml demin. water.

AHA stock solutions were prepared according to the following protocol. Five grams of l-lactic acid (Boom Chemie, Netherlands) and five grams glycolic acid (Merck, Germany) were each dissolved in 80 ml water, adjusted to pH 4.0 with 25% NaOH after which water was added to 100 ml to give 5% solutions of l-lactic acid and glycolic acid, respectively. Five grams of salicylic acid (Acros, Belgium) was dissolved in 80 ml water and adjusted to pH 4.4 (dissolution at pH 4.0 was not possible) with 25% NaOH after which water was added to 100 ml to give a 5% solution of salicylic acid.

Phosphate buffer pH 7.0 and citrate HCl buffer pH 4.0 were obtained from Merck, Germany.

Experiment

Five glass vials containing 0.1 gram serine protease solution, five glass vials containing 0.1 gram of aspartic proteinase and five glass vials containing 0.1 gram cysteine proteinase solution were prepared.

To each series of five vials was added 0.9 ml of respectively buffer pH 7.0, buffer pH 4.0, 5% 1-lactic acid, 5% glycolic acid and 5% salicylic acid. After mixing of enzyme and buffer or acid, a 40 microliter sample of each one of the fifteen solutions was applied in a matrix to Agfapan APX100 photographic film. The film with samples was then incubated for 1 hour in a wetted and covered petridish at 37° C. After incubation the photographic film was extensively rinsed with tap water and dried. Removal of the gelatin layer was used as a measure for proteolytic activity.

From the results obtained (see FIG. 2), it appeared that serine protease was only active around pH 7.0 and not at pH values around 4.0, either in the presence or absence of the various AHA's.

Whereas aspartic proteinase was not active at pH 7.0 or at pH 4.4 in the presence of salicylic acid, the enzyme was fully active at pH 4.0 with or without 5% 1-lactic acid or 5% glycolic acid.

Cysteine proteinase is active at pH 7.0 and at lower pH values in the presence of either l-lactic, glycolic or salicylic acid. Surprisingly low proteolytic activity was recorded at pH 4.0 in the absence of either one of the AHA's.

Conclusions

In combination with low pH values and AHA's, aspartic proteinases are preferred over serine proteases.

Cysteine proteinase from papaya exhibits proteolytic activity at both neutral and acidic pH values.

Depending on the conditions, the most appropriate proteolytic enzyme should be selected.

EXAMPLE 4

Enzymatic Activation of Ascorbyl Phosphate

Three different enzymes with a documented fosfatase activity were formulated in 70% propylene glycol and incubated under various conditions with magnesium ascorbyl phosphate. Dephosphorylation of magnesium ascorbyl phosphate was quantitated using 600 MHz proton NMR.

Enzymes

Phytase (*Aspergillus niger*; without glycerol, containing approx. 12.000 FTU/gram) as well as acid phosphatase (*Aspergillus niger*; lyophilized powder, containing approx. 10.000 units/gram) were obtained from Gist-brocades, Delft, the Netherlands.

Potato phosphatase (lyophilized powder) was obtained from Sigma.

Experiment

In a liquid containing 70% (w/w) propylene glycol in $D_2O$ and 2 mmol/l of EDTA (pH7–8), approx. 1% (w/w) of each of the above mentioned enzyme preparations was dissolved.

Ten times dilution of these enzyme stock solutions in $D_2O$, containing 1 (w/w) magnesium ascorbyl phosphate (NIKKO Chemicals Co, Japan), buffered to pH 5.0 using acetic acid and kept at 37° C., resulted in a 50% degradation of magnesium ascorbyl phosphate within a period of 4 hours.

Storage of the 70% propylene glycol containing enzyme stock solution at 37° C. for 1 week, did not markedly affect enzyme activity in this assay.

Combination of enzyme and substrate in the presence of 70% (w/w) propylene glycol, clearly demonstrated inactivity of the enzyme under these conditions. Starting from a stock solution of 5% (w/w) magnesium ascorbyl phosphate in D2O, a mixture was prepared containing:

70% (w/w) propylene glycol

1% (w/w) magnesium ascorbyl phosphate 2 mmol/l EDTA pH 7–7.5

After complete dissolution (during which a gel-like structure was formed), 1% (w/w) of (pre-dissolved) acid phosphatase and potato phosphatase enzyme was added. The resulting mixture was incubated for 1 week at 37° C. after which the concentration of hydrolysed magnesium ascorbyl phosphate was measured versus a similar sample containing no enzyme.

As no enzymatic hydrolysis could be detected, this demonstrates once more the lack of enzymatic acitivity in the presence of high concentrations of polyol.

EXAMPLE 5

Performance of Phytase Towards Magnesium Ascorbyl Phosphate Hydrolysis Under Application Conditions It is shown that phytase (NatuPhos® 5000L, Gist-brocades, Delft, the Netherlands) is effective under application conditions. In the test, 2 ml of 1% magnesium ascorbyl phosphate in 100 mM Na-acetate pH 6.0 was mixed with 200 µl enzyme solution. The enzyme solution was obtained by diluting NatuPhos® 5000L one to five in a solution containing 70% glycerol (to obtain 377 U/g magnesium ascorbyl phosphate; 1 U is the amount of enzyme liberating 1 µmol phosphate per minute from 1% vitamine C-phosphate at pH 6.0 and 30° C.). After different incubation times, the reaction was terminated by the addition of 1 ml 20% TCA.

The conversion of magnesium ascorbyl phosphate was followed by measuring the phosphate concentration using $^{31}$P-NMR. It could be shown that at 30° C. a 85% conversion of magnesium ascorbyl phosphate was obtained within 30 minutes. At 37° C., a conversion of 89% was obtained in the same period. After 60 min. incubation the yield increased up to around 90%. The minimal activity needed for complete conversion within 30 minutes was 122 U/g vitamin C-phosphate.

EXAMPLE 6

Enzymatic Hydrogen Peroxide Generation

Alcohol oxidase (Hansenula sp. from Sigma) powder with low concentrations of catalase was dissolved in water after which glycerol was added to obtain a final glycerol concentration of 60% (w/w). After storage of this stabilized enzyme solution for one month at room temperature, the enzyme solution was diluted ten times in an aqueous solution containing 2% of ethanol and 0.01 M phosphate pH 7. Formation of hydrogen peroxide was demonstrated by a green-blue color developing upon immersion of a Perid teststrip (Boehringer Mannheim, Germany) into the aqueous ethanol solution. The hydrogen peroxide thus generated can subsequently be used as a substrate for a peroxidase.

By incorporating a hydrogen peroxide generating enzyme and a suitable peroxidase such as lactoperoxidase (Sigma) in a stabilizing liquid in the one container and the required enzyme precursors in the other container, the active biocidal compound is obtained upon mixing of the content of the two containers according to the method of the invention.

EXAMPLE 7

Deacetylation of Vitamin A-acetate

Enzymes

Piccantase concentrate (*Rhizomucor miehei*, containing approx. 30.000 BGLE/g) was obtained from Gist-brocades, Séclin, France).

Maxatase pure (*Bacillus subtilis*, containing approx 2.16 BYU/kg) was obtained from Genencor International B.V., Delft, Netherlands.

G999 Phospholipase L (*Aspergillus niger*, containing approx 000 u/g) was obtained from Enzyme Bio-Systems Ltd., Englewood Cliffs, N.J., U.S.A.

Xylan acetylesterase (*A. niger* transformant TrA10 as described in EP0507369 and available through deposited microorganisms). After inoculation, transformant TrAl0 was grown on a culture medium containing 30 grams of soy pulp per liter to induce enzyme activity. After 48 hrs of growth at 30° C. under aeration and a minumum pH value of 4.0, the fermentation broth was centrifuged and the supernatant was filtered. First filtration was over Seitz K700 filters, second filtration over Seitz Supra 250 filter and germ filtration over a Seitz Supra EKS. The resulting liquid was concentrated by a factor 10 using ulta-filtration after which the concentrate was lyophilized. Xylan acetylesterase activity in the final powder was estimated to be approx. 300 units/gram powder.

Retinol-acetate Hydrolysis

Enzyme solutions were prepared by dissolving 6 milligrams of enzyme powder (i.e. Piccantase, Maxatase and Xylan acetylesterase) in one milliliter of demin. water. Of the liquid G999 preparation, 16 microliters were diluted in one milliliter of demineralized water. A stock solution of retinol acetate (Sigma) was prepared by dissolving 55 milligram retinol acetate in one milliliter of methanol.

Enzyme incubations were carried out by adding 100 microliter phosphate buffer pH 5.5; 100 microliter of enzyme solution and 200 microliter of retinal acetate stock solution to 500 microliter of demineralized water. After mixing, the various solutions were incubated under argon at 37° C. for either 1 or 4 hrs. Subsequently the solutions were lyophilised and deuterated chloroform (Merck, Germany) was added. Removal of the acetate part of retinal acetate was measured using 600 MHz proton NMR.

| Enzyme | Hydrolysis of retinol acetate | |
|---|---|---|
| | After 1 hr. | After 4 hrs. |
| Maxatase | − | − |
| G999 | − | + |
| Xylan acetylesterase | 0 | ++ |
| Piccantase | + | ++ |

− = no hydrolysis; 0 = detectible hydrolysis; + = significant hydrolysis; ++ = complete hydrolysis Lipid Hydrolysis In some applications of esterified vitamins, reactivation of the vitamins by enzymes with lipolytic activities is less desirable. For example during reactivation of vitamin precursors included in cosmetics, enzymic degradation of the oils included in the cosmetic product should be avoided. In this respect it would be advantageous to avail of vitamin activating enzymes with no degradative effect towards triglyceride oils. To establish the triglyceride degrading effect of the retinal acetate degrading enzymes mentioned above, the three active enzymes were subjected to a test in which hydrolysis of emulsified olive oil was quantitated.

An emulsion of olive oil in polyvinyl alcohol and water was prepared. Oil droplets larger than 10 microns do not occur. After addition of the enzym solution, the drop of pH created by the enzymatic liberation of fatty acids is compensated by a constant titration with sodium hydroxide. After a fixed incubation period at pH 7.5 and 37° C., the total quantity of sodium hydroxide used is measured and used as a (relative) value for lipolytic activity. The details of this method have been described in document CQA 4047 and can be obtained from Gist-brocades, Séclin, France, upon request.

| Enzyme | Lipolytic activity/gram enzyme |
|---|---|
| G999 | <1 |
| Xylan acetylesterase | 110 |
| Piccantase concentrate | 20.000 |

Conclusion

Various enzymes including lipases are able to deacetylate vitamin A-acetate.

Both G999 and Xylan acetylesterase are of particular interest because these enzymes combine deacetylation activity with very low lipolytic activity. Moreover, the natural substrates for these enzymes (i.e. lysophospholipids and acetylated xylans) do not normally occur on the human skin.

EXAMPLE 8

Suspension of Crystalline Protease

In multiple dose dispensing systems, proper suspension of the immobilized and stabilized material is important to guarantee an even dosing of the active material into the final composition. The suspension method should enable long term storage without sedimentation of the immobilized active material.

Materials

ChiroCLEC-BL, an aqueous solution of cross-linked protease (subtilisin) crystals, obtained from Altrus Biologics Inc., Cambridge, Mass, USA.

Carbopol-Ultrez-10, a viscosifying polymer, was obtained from BF Goodrich, The Hague, Netherlands.

From a homogeneous aqueous suspension of ChiroCLEC-BL, a sample of 4.8 grams was obtained and centrifuged to collect the crystalline material. After removal of the supernatant, the crystals were washed once in demineralized water and recentrifuged, after which the crystals were suspended in a final amount of 10 grams of a composition containing 35% glycerol, 35% butylene glycol and 0.4% Carbopol. The pH of the resulting suspension was adjusted to 5.5 using triethanolamine.

After thorough homogenisation the suspension was placed at 40° C. No sedimentation of the crystals was observed after a one month incubation at this temperature. Final dilution of the enzyme suspension restores enzymatic activity.

EXAMPLE 9

Stabilization of Dihydroxyacetone

The stability of DHA solutions was analyzed at different temperatures and pH values and with different antioxidant additions.

NMR Analysis

Identification as well as quantification of DHA degradation products was performed on a Bruker AMX-600 spectrometer, operating at a $^1H$ frequency of 600 Mhz. A 5 mm inverse probe was used. The huge water signal was suppressed by means of simple presaturation (2 s) or by means of presaturation with composite pulses (2 s). The delay of 2 s does not allow for complete relaxation between observe pulses, and therefore quantitative results should be considered as semi-quantitative, i.e. a systematic error may occur of up to 100%. However, the results within one series of measurements can be used for a meaningful comparison.

HPLC Analysis

Some samples were analysed by means of HPLC. To 2 ml of each sample 400 μl 20% perchloric acid was added. The following equipment and conditions were employed:

| HPLC pump | Varian LC 5010 |
|---|---|
| Injection volume | 20 μl |
| Detectors | IOTA differential refractometer |
| | Varian UV-5, 215 nm |
| Column | Aminex Hpx 87 H 300 × 7.8 mm |
| Eluens | 0.01 N $H_2SO_4$ |
| Flow | 0.6 ml/min |

This method was only used to quantify DHA in the experiments of series 1.

DHA Degradation in Water of 50° C.

Solutions were prepared of 5% DHA in a buffer solution of either 0.1 M phosphate (pH 7) or 0.1 M pyrophosphate (pH 5.5 and pH 8.5) in $D_2O$. In some cases ascorbic acid was added. Samples were incubated in a stove at 50° C. for up to 7 days.

DHA degradation 50° C. in water, sample conditions and residual DHA after 2, 5 and 7 days:

| Ascorbic acid | | DHA (g/l) after days of incubation | | | | Final |
|---|---|---|---|---|---|---|
| pH | g/l | 0 | 2 | 5 | 7 | pH |
| 5.5 | — | 49 | 31 | 22 | 17 | 4.9 |
| 7.0 | — | 49 | 18 | 13 | 11 | 5.6 |
| 8.5 | — | 46 | 2.4 | 1.1 | 0.8 | 7.5 |
| 7.0 | 9 | 48 | 18 | 13 | 11 | 5.7 |
| 5.7 | 9 | 47 | 28 | 19 | 14 | 5.3 |

Conclusions

Acidic pH conditions improve the storage stability of DHA.

The presence of a reducing agent like ascorbic acid has no significant effect on the storage stability of DHA.

DHA Degrdation at 40° C. Under Various Conditions

Solutions were prepared of 5% DHA in a buffer solution of 0.2 m pyrophosphate. To all samples 10% of $D_2O$ was added, containing t-butanol, which served as an internal standard. The final concentration of t-butanol was 0.45 mg/ml. Samples nr. 4 and 5 were prepared in a mixture of $H_2O$/glycol =1/1. Moreover, 10% t-butanol was added to these samples and in the case of sample nr. 5 also 15 mg (dl) α-tocoferol. Samples were flushed with $N_2$ gas or air for 30 minutes. These conditions are also summarised underneath. Samples were incubated at 40° C. for 35 days.

Sample composition and treatment:

| Sample nr | DHA | pH | flush | additions |
|---|---|---|---|---|
| 1 | 5 | 6 | air | — |
| 2 | 5 | 6 | $N_2$ | — |
| 3 | 5 | 5 | air | — |
| 4 | 5 | 5 | $N_2$ | glycol/$H_2O$/t-bu 45/45/10 |
| 5 | 5 | 5 | $N_2$ | see 4 + 0.3 tocoferol |
| 6 | 5 | 2.6 | air | — |

DHA degradation after 35 days at 40° C.:

| Sample nr. | Remaining DHA initial = 100% | ppm formic acid formed | ppm acetic acid formed |
|---|---|---|---|
| 1 | 20% | 1600 | 2400 |
| 2 | 20% | 1400 | 2600 |
| 3 | 40% | 1000 | 1200 |

-continued

| Sample nr. | Remaining DHA initial = 100% | ppm formic acid formed | ppm acetic acid formed |
| --- | --- | --- | --- |
| 4 | 30% | nd | nd |
| 5 | 30% | nd | nd |
| 6 | 90% | 200 | 300 | na: not determined

Conclusions:

Significant stabilisation of DHA can only be obtained by adjusting the pH to very low values.

EXAMPLE 10

Natamycin in Shampoo

In this example the use of a dispensing system is described which is designed to simultaneously deliver a natamycin containing composition and a shampoo composition in a ratio of 1:10.

11 g of natamycin trihydrate, 1 g of xanthan gum (Keltrol® RD, Kelco International Limited), 8 g of lactose, 0.5 g of citric acid and 0.055 g of sodiumcitrate dihydrate were mixed together in a Turbula® mixer. The total mixture was then suspended into 480 ml of water. The resulting suspension had a pH of 4.8 and contained 2% of pure natamycin.

25 ml of the above suspension was put into one compartment of the dispenser, while the other compartment was filled with 225 ml of a shampoo composition.

At the application, a shampoo dosage containing 2000 ppm of natamycin was obtained.

EXAMPLE 11

Natamycin for Trichophyton 110 g of natamycin trihydrate and 1 g of xanthan gum were suspended in 388 ml of distilled water and then sterilized by heat treatment. The pH of the suspension was 6.5. After standing for at least 4 weeks no sedimentation was observed. HPLC analysis showed that the natamycin content immediately after the preparation and after 4 weeks storing at ambient temperature was respectively 20.1 and 20.2% (w/w).

200 g citric acid monohydrate and 4 g of xanthan gum were dissolved in 876 ml of distilled water and sterilized by heat treatment. The pH of the solution was 3.0.

By using a dispensing system which is designed to simultaneously deliver the natamycin composition and the citric acid solution in a ratio of 1:9, each dosage contains about 2% of natamycin. To obtain a solution containing 200 or 100 ppm of natamycin for the treatment of the animals, the dosage may be simply diluted 100 to 200 times by mixing with water. Thus a dispenser containing 250 g of the sample (25 g of the natamycin suspension and 225 g of the citric acid solution) will be sufficient for making an overall quantity of 25 to 50 l of the treatment solution.

By using a dispensing system which is able to simultaneously deliver a stable natamycin-containing suspension and a citric acid composition, both compositions being separately contained, a system is obtained which conveniently enables the cost-effective preparation of small dosages.

EXAMPLE 12

Dispensing Systems

Dispensing systems suited for simultaneously dosing two separately contained incompatible compounds, are well known. As such, the dispensing system schematically depicted in FIG. 3 (dispenser from Maplast, Italy) is just one example out of a number of products which range from small, two-chambered single use pouches to tubes using different product compartments or tubes compartmentalized using extrudable, viscous and relatively inert materials to separate the incompatible compounds.

Figure 3:
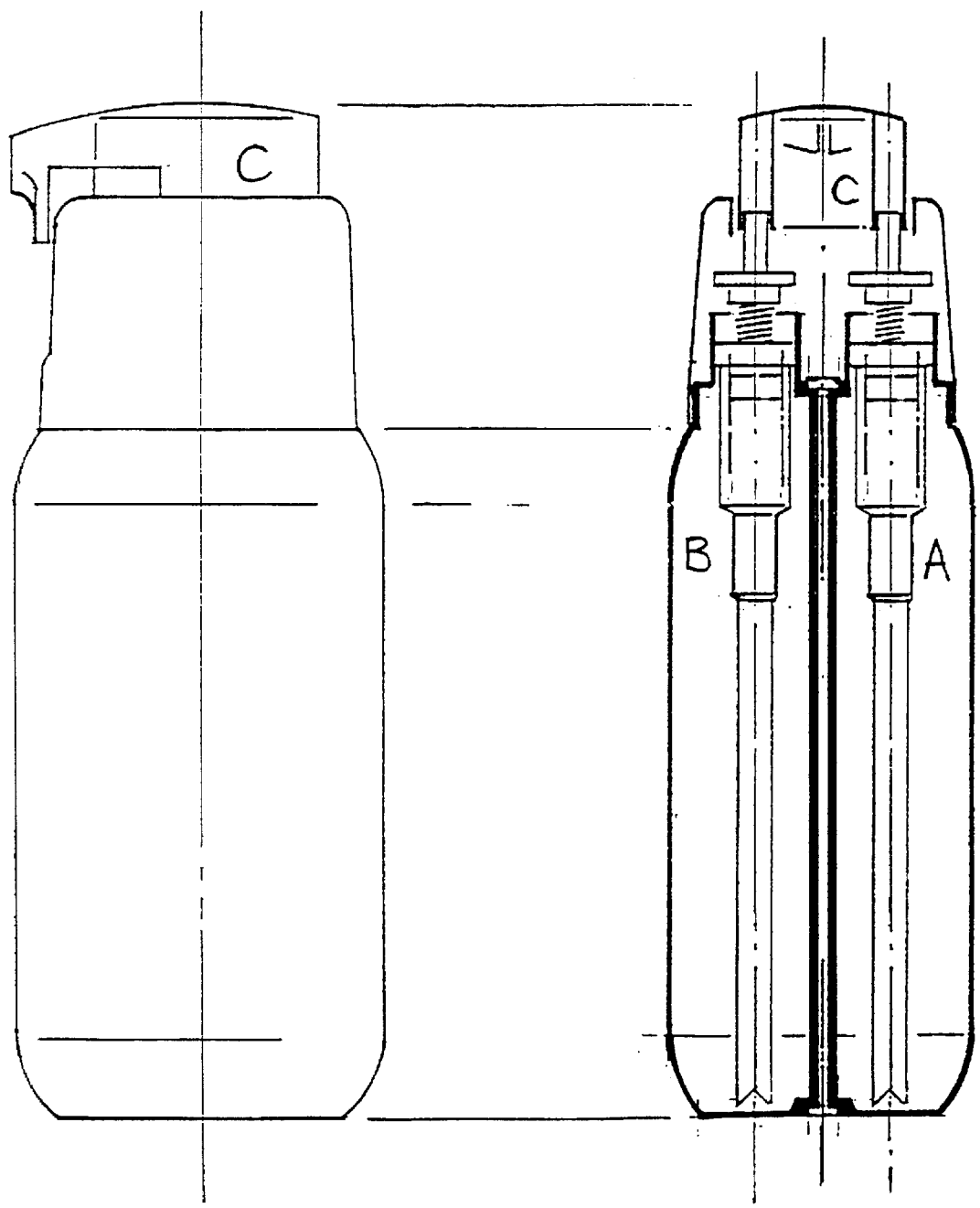
FIG. 3 shows a dispensing pump in which two compositions are separately contained. The two compositions are simultaneously dispensed and can be mixed within the dispensing pump or can be delivered separately and mixed in situ.

The dispenser shown in FIG. 3 is able to simultaneously dose two compounds separately contained in A and B by pressing dosing head C. Pressing dosing head C activates two small pumps which subsequently dispense the two compounds in approximately equal volumes. Depending on the design of the dosing head, the compounds can be dosed in two separate streams or in just one stream.

According to the present invention, a dispensing unit is required that is able to deliver a stabilized, aqueous enzyme composition together with a non-enzyme containing basic composition in a ratio of for instance 1:2.

Figure 2:
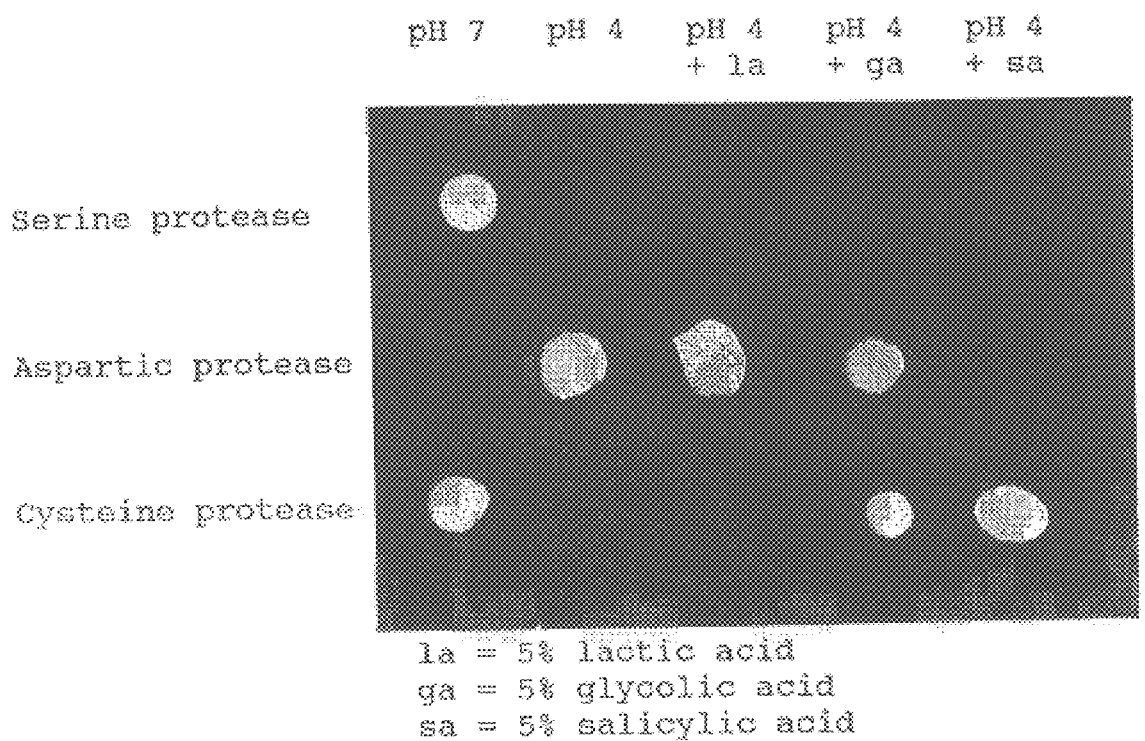
FIG. 2 shows the proteolytic activity of different proteases at a pH of 4 and 7 and in the presence of $\alpha$-hydroxy acids.

Translated to the dispenser depicted in FIG. 2, this would mean that one of the two pumps is able to dose at least twice the volume of the other pump in just one stroke of dosing head C.

Translated to a two-chambered single use pouch, this would mean that the chamber containing the enzyme composition contains at least half as much product volume as the other chamber.

Translated to a two-compartment tube, this would mean that under equal pressure the discharge orifice for the compartment containing the composition without enzyme allows the passage of at least twice as much product as the discharge orifice of the other compartment.

Translated to a tube which is compartmentalized using extrudable material, this would mean that the composition without enzyme is present inside the tube in at least double the volume of the enzyme-containing product.

What is claimed is:

1. A dual chamber dispensing system for the simultaneous dosing of two aqueous compositions comprising first and second separate chambers that respectively contain a first aqueous composition in said first chamber and a second aqueous composition in said second chamber and dispensing means that cause the simultaneous dosing of said two aqueous compositions to obtain a final composition that is directly applied; wherein, said first composition is a stable formulation of an enzyme in the presence of a polyol;

said second composition is an aqueous composition, which reactivates the enzyme;

said final composition contains an effective concentration of said reactivated enzyme; and said first composition and said second composition are dispensed in a ratio from about 1:1 to about 1:50.

2. The dispensing system of claim 1, wherein said means dispenses said first composition and said second composition in a ratio from about 1:2 to about 1:20.

3. The dispensing system of claim 2, wherein said means dispenses said first composition and said second composition are dispensed in a ratio from about 1:5 to about 1:10.

4. The dispensing system of claim 1, wherein said second composition contains an additional active ingredient.

5. The dispensing system of claim 1, wherein said first composition additionally contains a viscosifying agent.

6. The dispensing system of claim 1, wherein said biologically effective compound is formulated in a particle form.

7. The dispensing system of claim 6, wherein said first composition additionally contains a viscosifying agent which forms a three-dimensional network in an aqueous composition.

8. The dispensing system of claim 6, wherein said particle form is a crystal.

9. The dispensing system of claim 8, wherein said first composition additionally contains a viscosifying agent which forms a three-dimensional network in an aqueous composition.

10. The dispensing system of claim 1, wherein said enzyme is formulated in a particle form.

11. The dispensing system of claim 10, wherein said particle form is obtained by immobilizing said enzyme on a solid carrier.

12. The dispensing system of claim 10, wherein said particle form is obtained by crystallization of said enzyme.

13. The dispensing system of claim 10, wherein said first composition additionally contains a viscosifying agent which forms a three-dimensional network in an aqueous composition.

14. The dispensing system of claim 1, wherein said second composition contains an active compound precursor which is a substrate for said enzyme.

15. The dispensing system of claim 14, wherein said precursor is a vitamin precursor.

16. The dispensing system of claim 1, wherein said polyol is present in said first composition in a concentration of about 20–90%.

17. The dispensing system of claim 16, wherein said polyol is present in said first composition in a concentration of about 30–90%.

18. The dispensing system of claim 17, wherein said polyol is present in said first composition in a concentration of about 40–90%.

19. The dispensing system of claim 18, wherein said polyol is present in said first composition in a concentration of about 50–90%.

20. The dispensing system of claim 19, wherein said polyol is present in said first composition in a concentration of about 60–80%.

21. The dispensing system of claim 1, wherein said enzyme is a protease.

22. The dispensing system of claim 1, wherein said enzyme is an esterase having a preference for lower chain acyl groups.

23. The dispensing system of claim 22, wherein said esterase has a preference for lower chain acyl groups having 1 to 9 carbon atoms.

24. The dispensing system of claim 1, wherein said enzyme is a phosphatase.

25. The dispensing system of claim 24, wherein said phosphatase is a phytase.

26. A method for topical application of a biologically effective compound comprising topically administering to a subject said enzyme contained in a carrier by simultaneous dosing two aqueous compositions from the dispensing system of claim 1.

* * * * *